United States Patent [19]
Rath et al.

[11] Patent Number: 5,650,418
[45] Date of Patent: Jul. 22, 1997

[54] THERAPEUTIC LYSINE SALT COMPOSITION AND METHOD OF USE

[75] Inventors: Matthias Rath, Woodside; Linus Pauling, Big Sur, both of Calif.

[73] Assignee: Therapy 2000, Woodside, Calif.

[21] Appl. No.: 217,348

[22] Filed: Mar. 24, 1994

Related U.S. Application Data

[63] Continuation of Ser. No. 58,992, May 6, 1993, abandoned, which is a continuation of Ser. No. 786,026, Oct. 31, 1991, abandoned, which is a continuation-in-part of Ser. No. 557,516, Jul. 24, 1990, Pat. No. 5,278,189, which is a continuation-in-part of Ser. No. 533,129, Jun. 4, 1990, abandoned.

[51] Int. Cl.$^6$ .................. A61K 31/44; A61K 31/355; A61K 31/34; A61K 31/195; A61K 31/07
[52] U.S. Cl. .................. 514/356; 514/458; 514/474; 514/562; 514/564; 514/725
[58] Field of Search .................. 514/474, 725, 514/458, 356, 564, 562

[56] References Cited

FOREIGN PATENT DOCUMENTS 6087221  10/1983  Japan.

OTHER PUBLICATIONS

*The Nutrition Desk Reference*, Garrison et al, Keats Publishing, 1985, pp. 172–180.

*Primary Examiner*—Raymond Henley, III
*Attorney, Agent, or Firm*—Ali Kamarei

[57] ABSTRACT

A therapeutic lysine-based composition and methods for its use in the prevention and treatment of cardiovascular disease is disclosed. The composition includes at least one ascorbate compound, nicotinic acid and at least one lysine compound. The ascorbate compound, nicotinic acid and the lysine compound are preferentially present in a ratio of 8:1:1. The composition may also include N-acetyl cysteine, a carotene and/or nicotinic acid. A patient at risk of developing or with a pre-existing cardiovascular disease is treated by administering orally or parenterally a desired dosage of the composition on a daily basis.

6 Claims, 3 Drawing Sheets

THERAPEUTIC LYSINE SALT COMPOSITION AND METHOD OF USE

This is a continuation of application Ser. No. 08/058,992, filed on May 6, 1993, now abandoned which is a Continuation of application Ser. No. 07/786,026, filed Oct. 31, 1991, now abandoned which is a continuation-in-part of application Ser. No. 07/557,516, filed Jul. 24, 1990, now U.S. Pat. No. 5,278,189 which is a continuation-in-part of application Ser. No. 07/533,129, filed Jun. 4, 1990, now abandoned.

FIELD OF THE INVENTION

The present invention relates generally to compositions effective in the prevention and treatment of cardiovascular disease and more particularly to compositions based on lysine and/or pharmaceutically acceptable salts of lysine.

References

Armstrong et al. 1986. Atherosclerosis 62:249–257.

Berg, K. 1963. Acta Pathologica 59:369–382.

Blumberg et al. 1962. J. Clin. Investigations 41:1936–1944.

Dahlem et al. 1986. Circulation 74:758–765.

Eaton et al. 1987. PNAS USA 84:3224–3228.

Gonzales-Gronow et al. 1989. Biochemistry 28:2374–2377.

Hajjar et al. 1989. Nature 339:303–305.

Harpel et al. 1989. PNAS USA 86:3847–3851.

McLean et al. 1987. Nature 300:132–137.

Miles et al. 1989. Nature 339:301–302.

Salonen et al. 1989. EMBO Journal 8:4035–4040.

Zenker et al. 1986. Stroke 17:942–945.

BACKGROUND OF THE INVENTION

Lipoprotein(a) ("Lp(a)") structurally resembles low density lipoprotein ("LDL") in that both share a lipid apoprotein composition, apolipoprotein B-100 ("apo-B"), the ligand by which LDL binds to LDL receptors present on the interior surfaces of arterial walls. (Berg, Blumberg) The unique feature of Lp(a) is an additional glycoprotein, designated apoprotein(a) ("apo(a)"), which is linked to apo-B by disulfide group. The cDNA sequence of apo(a) shows a striking homology to plasminogen, with multiple repeats of kringle 4, one kringle 5, and a protease domain. The isoforms of apo(a) vary in range of 300 to 800 kD and differ mainly in their genetically determined number of kringle 4 structures. (McLean) Apo(a) has no plasmin-like protease activity. (Eaton) Serine protease activity, however, has been demonstrated. (Salonen) Like plasminogen, Lp(a) has been shown to bind lysine-sepharose, immobilized fibrin and fibrinogen, and the plasminogen receptor on endothelial cells. (Gonzales-Gronow, Hajjar, Harpel, Miles) Furthermore, Lp(a) has been demonstrated to bind to other components of the arterial wall like fibrinectin and glycosaminoglycans. The nature of these bindings, however, is poorly understood.

Essentially all human blood contains Lp(a). There can, however, be a thousand-fold range in its plasma concentration between individuals. High levels of Lp(a) are associated with a high incidence of cardiovascular disease. (Armstrong, Dahlem, Miles, Zenker) The term "cardiovascular disease" is intended to refer to all pathological states leading to a narrowing and/or occlusion of blood vessels throughout the body, but particularly atherosclerosis, thrombosis and other related pathological states, especially as occurs in the arteries of the heart muscle and the brain.

For some time, conventional medical treatment of cardiovascular disease has focused on LDL, the so called "bad cholesterol," and strategies for lowering its concentration in the bloodstream. A great many studies have been published ostensibly linking cardiovascular disease with elevated levels of LDL. As a result, most therapies for the prevention and treatment of cardiovascular disease rely on drugs that reduce serum levels of LDL in the bloodstream. More recent studies have found the beneficial effects of lowering LDL levels to be somewhat equivocal. Thus, the efficacy of these drugs and therapies continues to be a source of major debate within the medical community.

There exists therefore a need for a drug therapy for preventing or treating cardiovascular disease by (i) reducing damage to blood vessel walls, thereby reducing the binding potential Lp(a) to blood vessel walls and thus diminishing the deleterious effects of high levels of Lp(a) in the bloodstream.

There further exists a need for a treatment that employs compounds that are safe to use with few if any complicating and undesired side effects.

SUMMARY OF THE INVENTION

It is an object of the invention to provide a pharmaceutical composition that is inexpensive, has few or no undesired side effects and is available without a doctor's prescription for the prevention and treatment of cardiovascular disease.

It is another object of the present invention to provide a method of prevention and treatment of cardiovascular disease that can be both prophylactic or therapeutic, depending upon the progression of disease within a particular patient.

It is yet another object of the invention to provide a method of preventing or treating cardiovascular disease that results in few if any undesired side effects and that is inexpensive to carry out.

According to one aspect of the invention, a lysine-based pharmaceutical composition is provided. The composition includes in addition to a lysine or salt thereof, one or more forms of ascorbic acid and tocopherol. More particularly, the composition also includes other compounds having an antioxidant effect such as carotene, N-acetyl cysteine and nicotinic acid.

In another aspect of the invention, a method for preventing or treating cardiovascular disease is described, comprising the step of administering to a subject a therapeutically effective amount of the lysine-based composition. The treatment has prophylactic value in that it tends to prevent oxidative damage to the interior walls of arteries, thereby decreasing the potential for Lp(a) binding and ultimately plaque accumulation. The treatment has therapeutic value in that it appears to halt and perhaps reverse the progress of arterial narrowing by inhibiting further binding of Lp(a) and perhaps by promoting the release of Lp(a) already bound.

These and other features and advantages of the invention will become more readily understood upon consideration of the following detailed description of the invention.

DETAILED DESCRIPTION OF THE INVENTION

Figure 1:
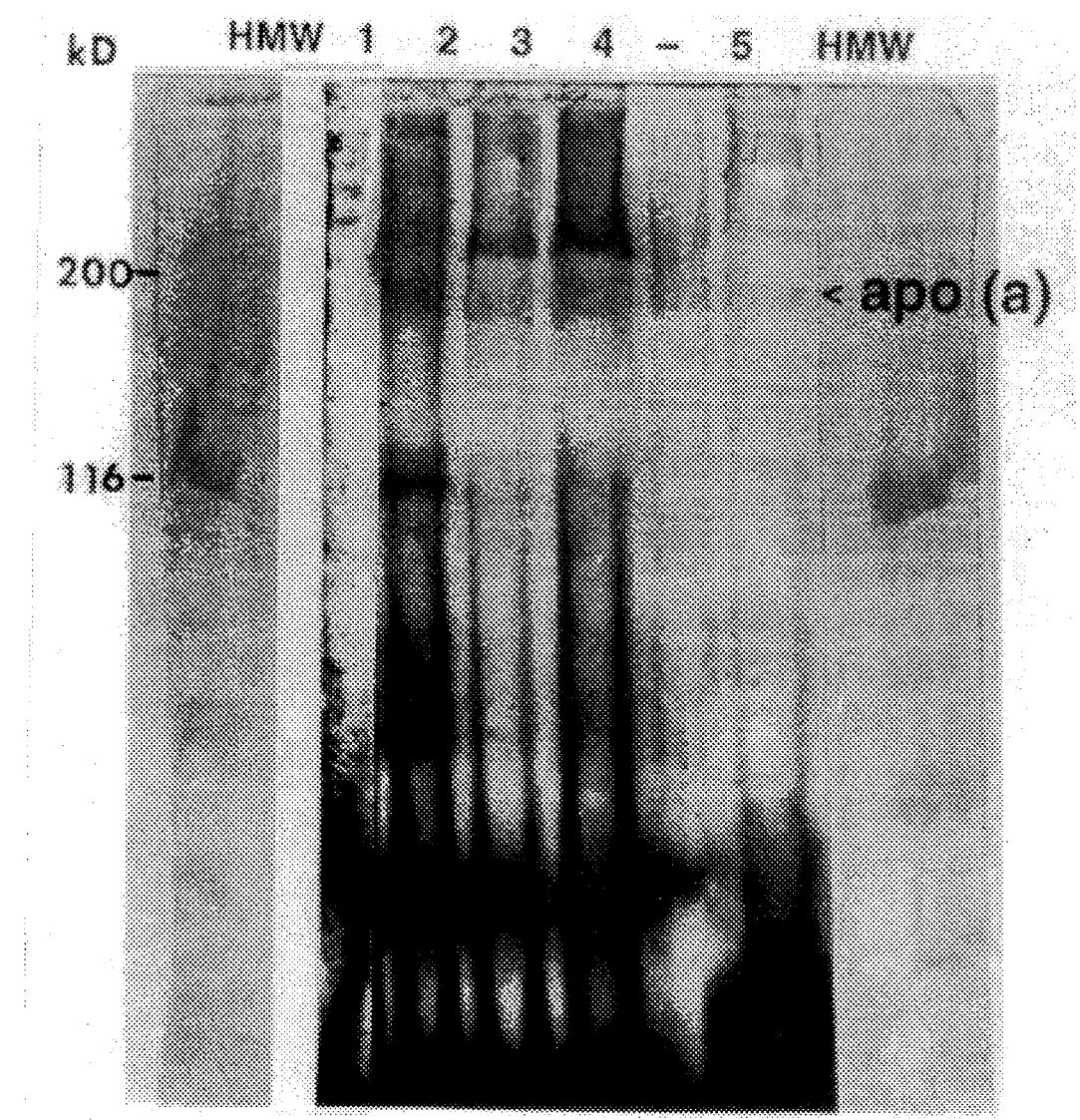
FIG. 1 is an immunoblot of the plasma of guinea pigs from the test described in Example 1.

Our invention is based in part on our discovery that animals that have lost the ability to produce ascorbate, such as higher primates and guinea pigs, uniformly produce Lp(a), whereas animals that possess this ability generally do not produce Lp(a). Further, we have found that ascorbate deficiency in humans and guinea pigs tends to raise Lp(a) levels and causes atherosclerosis through deposition of Lp(a) on the inner surface of the arterial wall.

We have also discovered that substances that inhibit binding of Lp(a) to components of the arterial wall, particularly to fibrinogen, fibrin and fibrin degradation products herein identified as binding inhibitors, such as lysine, cause release of Lp(a) from the arterial wall. Thus, ascorbate and such binding inhibitors are not only useful in the prevention of cardiovascular disease, but also for the treatment of such disease. The present invention provides a novel pharmaceutical composition based on lysine that is safe to use and available without a doctor's prescription. This compound can be used in a method to slow or prevent the onset of cardiovascular disease, as well as slow, stop or even reverse the progress of the disease.

A. Lysine-Based Composition.

According to one aspect of the present invention, a pharmaceutical composition based on a lysine compound is provided. In one embodiment, the composition comprises a combination of an ascorbate compound, nicotinic acid and a lysine compound, along with a pharmaceutically acceptable carrier.

The ascorbate compound may be ascorbic acid, a pharmaceutically acceptable form of an ascorbate salt or a mixture thereof. The lysine compound may be lysine in its electrically neutral form or a pharmaceutically acceptable salt of lysine. Some acceptable salt forms of lysine include lysine hydrochloride, lysine dihydrochloride, lysine succinate, lysine glutamate, and lysine orotate.

The relative percentages of each class of compounds in the compositions may be varied to some degree, although ascorbate should be present in amounts several times greater than either nicotinic acid or lysine compounds. A preferred ration of ascorbate to nicotinic acid to lysine is 4:1:1. It will be understood that each class of compound may be present exclusively in one chemical form, or may be present as a mixture of chemical forms as set forth and described above.

In addition to ascorbate, nicotinic acid and lysine, it is preferred to add other vitamins and compounds with demonstrated antioxidative properties. Thus, in another embodiment of the composition of the invention, carotene and tocopherol may be added.

It will also be appreciated that the composition just described may consist of a simple mixture of the individual compounds described, or they may be covalently linked or present as ionically bound salts of one another. For example, ascorbate may be covalently linked to lysine.

The constituents described above are generally mixed with a pharmaceutically acceptable carrier, to form tablets or capletts for oral administration. The carrier may contain a binder such as tragacanth, corn starch or gelatin; a disintegrating agent, such as alginic acid, and/or a lubricant such as magnesium stearate. If administration in liquid form is desired, use of sweetening and/or flavoring agents may be used. It will be understood that the composition of the invention may also be delivered parenterally by injection or IV, wherein the carrier may be an isotonic saline solution, a phosphate buffered solution or similar carrier.

B. Methods of Use.

The composition described above may be used as a prophylactic agent to halt or delay the onset of cardiovascular disease or may be employed to treat an existing cardiovascular condition.

In the case of preventative treatment, it is preferred to administer a composition containing ascorbate, nicotinic acid and a lysine compound to block any initial Lp(a) binding with the arterial wall, as well as to prevent damage to the vessel wall resulting from a degeneration of the extracellular matrix. In another teatment, both tocopherol and a cavotene, preferably β-caotone, are added. Table I sets forth preferred ranges of dosages of the individual components of the composition of the present invention. The protocol for prophylactic treatment of patients at risk for cardiovascular disease calls for administration of the doses listed in Table I on a daily basis. Because ascorbate is so quickly cleared from the system, and because it can be irritating to the intestinal lining in high doses until tolerance is reached, it may be preferable to divide the preferred dose into two to four smaller doses that can be administered with meals.

TABLE I

DOSAGES OF COMPONENTS OF THE
DRUG COMPOSITION OF THE INVENTION

| Component | Oral Administration Dosage † | Parenteral Administration Dosage † |
| --- | --- | --- |
| Ascorbate | 5–2500 | 25–2500 |
| Lysine | 5–300 | 5–500 |
| Nicotinic Acid | 1–300 | 1–300 |
| Tocopherol | 1–50 | 1–50 |
| Carotene | 1–300 | 1–300 |

†mg/kg of body weight per day

In the treatment of an existing condition of cardiovascular disease, it will be understood that the therapeutic composition described above should include at least ascorbate, nicotinic acid and lysine but with each in a higher dosage. It is also preferred to add a carotene and tocopherol as additional antioxidants. Suitable dosages are listed in Table I. It should be noted that the concentrations of the individual constituents vary, depending on whether administration is oral or parenteral, and depending on the severity of the disease. It will be appreciated therefore that a subject diagnosed with advanced stages of atherosclerosis should receive a dosage at the higher end of the ranges set forth in Table I.

The composition of the present invention is also useful in the treatment of diseases arising from a degeneration of the extracellular matrix, particularly metastasis of cancel. While not wishing to be bound by a particular theory of operation, it appears that lysine is available to inhibit both plasminogen and plasmin, which eventually stimulates the production of collagenase and, ultimately, the collagen network in the extracellular matrix. Such degradation also exacerbates advances cases of atherosclerosis. Thus, lysine is effective not only to block potential Lp(a) binding sites, but also to inhibit the action of certain proteolytic enzymes that may ultimately result in damage to arterial walls. Thus, in another embodiment of the present invention, natural inhibitors of proteolytic enzymes, such as are found in soybeans, may be added to the composition.

Experimental

Having disclosed the preferred embodiment of the invention, the following examples are provided by way of illustration only and are not intended to limit the invention.

Guinea pigs are similar to man in their inability to synthesize ascorbate and in their ability to synthesize Lp(a). Guinea pigs are therefore selected as a suitable test animal to test the compositions and methods of the present invention.

Example 1A: Guinea Pig Study Model
Development of Atherosclerosis in Female Guinea Pigs Three female Hartley guinea pigs with an average weight of 800 gm and an approximate age of 1 year were selected for study. One animal received an extreme hypoascorbic diet with approximately 1 mg ascorbate per kg body weight per day. One of the other animals received a diet containing 4 mg ascorbate per kg body weight per day. The remaining animal served as a control and received 40 mg ascorbate per kg body weight per day.

Once after ten days and then again after three weeks, blood was drawn by ear puncture from the anaesthetized animals and collected into EDTA containing tubes. Subsequent to drawing blood at the three weeks, the animals were sacrificed. Plasma was stored at −80° C. until analysis could be conducted. Lp(a) was detected in the plasma by use of an SDS-polyacrylamide gel according to the techniques of Neville (J. Biol. Chem. 257:13150–13156. 1982), the contents of which are incorporated herein by reference. Forty µL of plasma and 20 mg of arterial wall homogenate were applied in delipidated form per lane of the gel.

Lp(a) presence in the gel was detected by immunological assay using polyclonal anti-human apo(a) antibody (available from Immuno, Vienna, Austria) followed by a rabbit anti-sheep antibody with subsequent silver enhancement (available from Bio-Rad). The determinations of cholesterol and triglycerides were conducted at California Veterinary Diagnostics (Sacramento) using the enzyme assay of Boehringer Mannheim. Plasma ascorbate concentration was determined by the dinitrophenylhydrazine method of Shaffer et al. (J. Biol. Chem. 212:59. 1955).

Figure 2A:
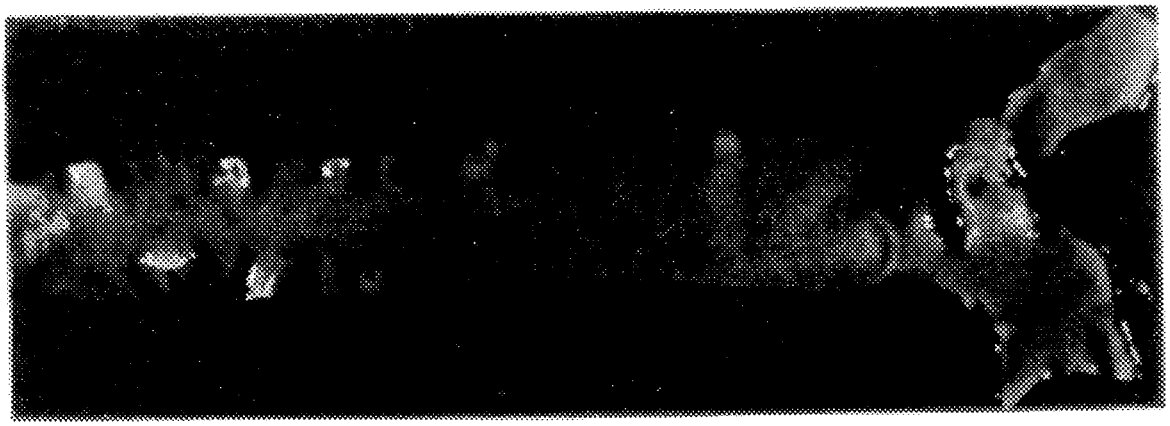
FIG. 2A is a picture of an aorta of a guinea pig that received an adequate amount of dietary ascorbate, as described in Example 1.
Figure 2B:
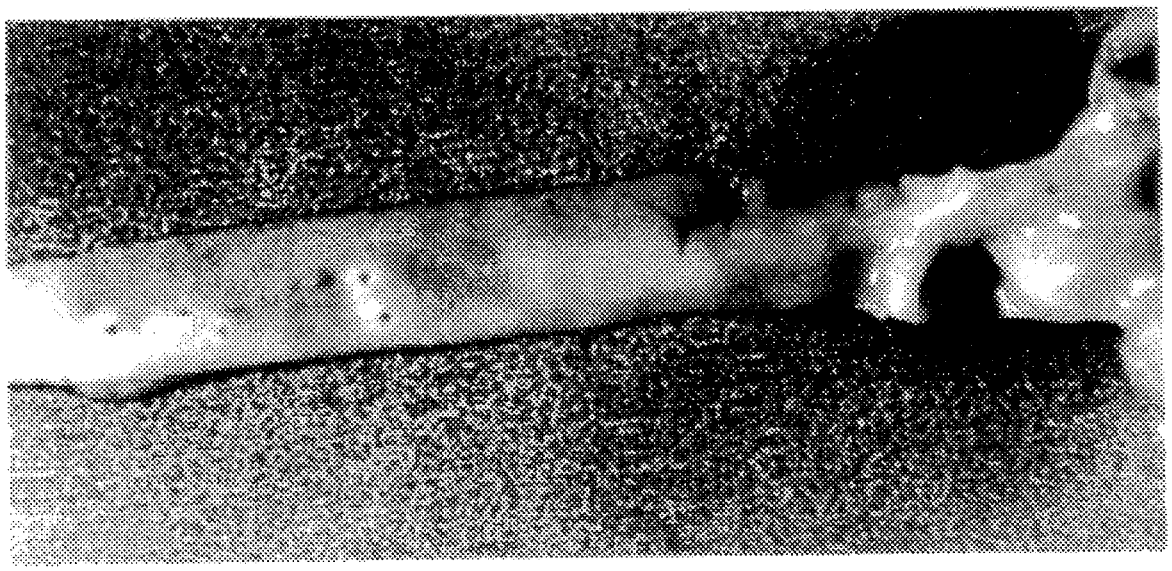
FIG. 2B is a picture of an aorta of a guinea pig receiving a hypoascorbic diet over a three week period, as described in Example 1.
Figure 3:
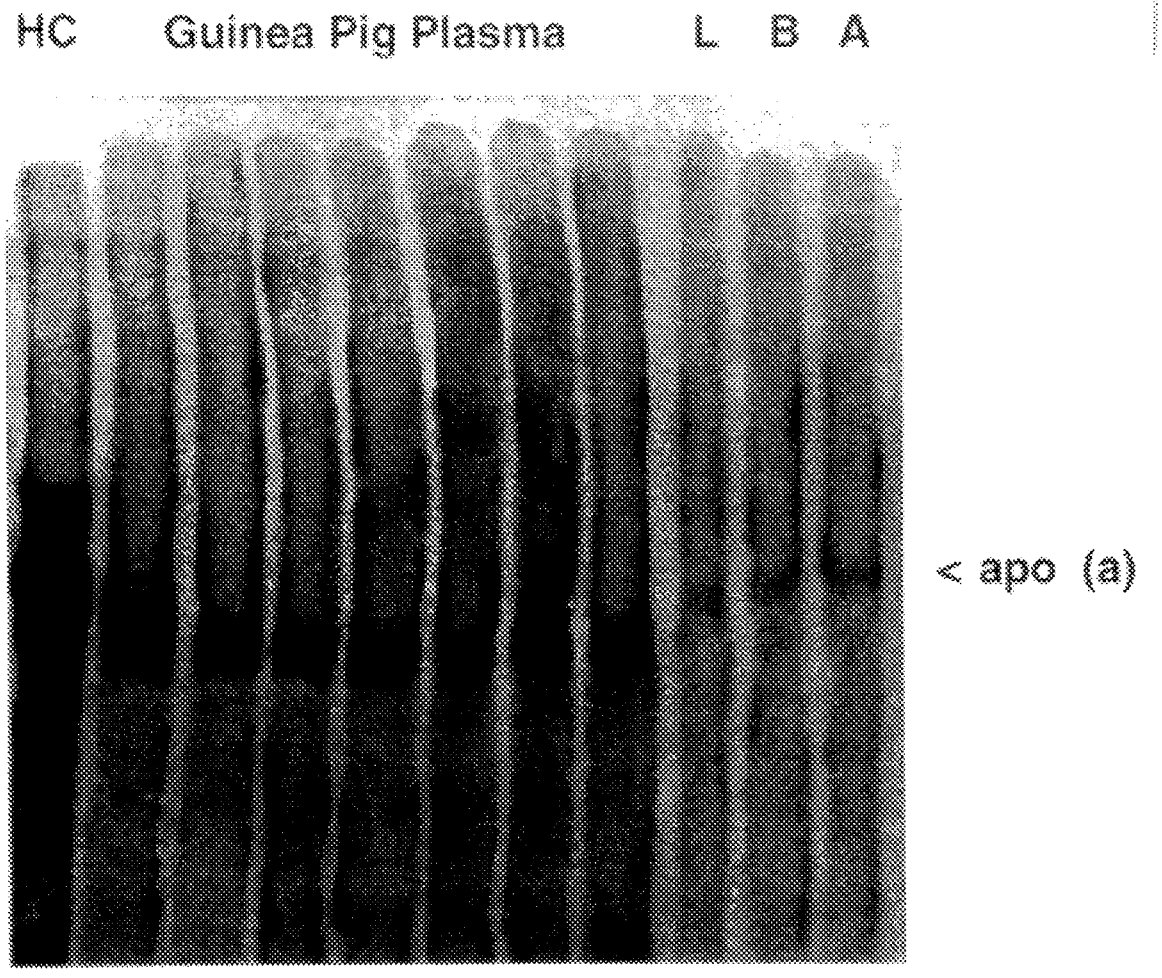
FIG. 3 is an immunoblot of plasma and tissue of guinea pigs receiving a variety of dietary intact of ascorbate, as described in Example 2.

Vitamin C deficiency in the diet led to an increase of Lp(a) in the plasma of the guinea pig, as indicated by a clear band in the immunoblot of the plasma after 10 and 20 days on a hypoascorbic diet (see FIG. 1). At necropsy the animals were anaesthetized with metophase and exsanguinated. Aorta, heart and various other organs were taken for biochemical and histological analysis. The aorta was excised, the adventitial fat was carefully removed, and the vessel was opened longitudinally. Subsequently the aorta was placed on a dark metric paper and a color slide was taken. The picture was projected and thereby magnified by an approximate factor of 10. The circumference of the ascending aorta, the aortic arch and thoracic aorta as well as the atherosclerotic lesions in this area were marked and measured with a digitalized planimetry system. The degree of atherosclerosis was expressed by the ration of plaque area in relation to the total aortic area defined. The difference in the 3 one-year old animals of the experiment was significant and pronounced lesions were observed in the ascending aorta and the arch of the ascorbate deficient animal (see FIG. 2b).

Example 1B: Guinea Pig Study Model
Development of Atherosclerosis in Male Guinea Pigs 33 male guinea pigs with a mean weight of 550 gm and an approximate age of 5 months were selected. One group of 8 animals served as a control and received 40 mg ascorbate per kg of body weight per day ("Group A"). To induce hypoascorbemia, 16 animals were fed a diet containing 2 mg of ascorbate per kg body weight per day ("Group B"). Group A and half of Group B were sacrificed after five weeks as described above. The remaining half of Group B was kept alive for 2 more weeks, receiving daily intraperitoneal injection of 1.3 gms of sodium ascorbate per kg body weight per day. After this period, these animals were sacrificed.

Plasma ascorbate levels were negatively correlated with the degree of atherosclerotic lesion. Total cholesterol levels increased significantly during periods of ascorbate deficiency (see Table II).

The aortas of the guinea pigs receiving a sufficient amount of ascorbate were essentially plaque free, with minimal thickening of the intima in the ascending region. In contrast, the ascorbate-deficient animals exhibited fatty streak-like lesions, covering most parts of the ascending aorta and the aortic arch. In most cases the branching regions of the intercostal arteries of the aorta exhibited similar lipid deposits. The difference in the percentage of lesion area between the control animals and the hypoascorbic diet animals was 25% deposition of lipids and lipoproteins in the arterial wall.

TABLE II

MEAN PLASMA PARAMETERS OF THE DIFFERENT GUINEA PIG GROUPS IN RELATION TO THE AREA OF AORTIC LESIONS

|  | Control | Scurvy (progress) | Regression (after scurvy) |
| --- | --- | --- | --- |
| Plasma cholesterol (mg/dl) | 39 | 54 | 33 |
| Total plasma ascorbic acid (µg/ml) | 5.03 | 3.01 | 20.64 |
| Atheroscl. lesion (as a % of aorta thoracic surface) | — | 25 | 19 |

Example 2

Effect of Lysine Composition on Disease

Human arterial wall tissue is obtained post mortem from the aorta ascendens of a patient suffering from cardiovascular disease showing an atherosclerotic lesion as evidenced by homogenous intimal thickening. The arterial wall is cut into pieces, with about 100 mg of the cut up tissue homogenized in a glass potter for 1 minute in 2.5 ml of an isotonic solution containing ascorbate alone, ascorbate combined with lysine. The arterial wall segments are then placed in the solution and allowed to incubate. The solution is then decanted off and the concentration of Lp(a) measured according to the techniques discussed above.

It is now apparent that the methods and compositions of the present invention meet longstanding needs in the field of prevention and treatment of cardiovascular disease. Although the invention has been described with respect to preferred embodiments, it will be apparent that various changes and modifications may be made without departing from the invention as set forth in the accompanying claims.

We claim:

1. A Pharmaceutical lysine-based composition consisting essentially of:
   (a) at least one ascorbate compound selected from the group consisting of ascorbic acid, pharmaceutically acceptable ascorbate salts and mixtures thereof;
   (b) nicotinic acid;
   (c) at least one lysine compound selected from the group consisting of lysine, lysine hydrochloride, lysine dihydrocholoride, lysine orotate, lysine succinate, and lysine glutamate; and
   (d) a pharmaceutically acceptable carrier, said composition in an amount effective to treat cardiovascular disease.

2. The composition of claim 1 wherein the ascorbate compound, nicotinic acid and lysine compound are present respectively in a ratio of 4:1:1.

3. A therapeutic dose of the composition of claim 2 consisting essentially of 400 mg of the ascorbate compound, 100 mg of nicotinic acid and 100 mg of lysine compound.

4. A Pharmaceutical lysine-based composition for the prevention of cardiovascular disease consisting essentially of:
   (a) at least one ascorbate compound selected from the group consisting of ascorbic acid, pharmaceutically acceptable ascorbate salts and mixtures thereof, said ascorbate present in an amount of 400 mg;
   (b) nicotinic acid present in an amount of 100 mg;
   (c) at least one lysine compound selected from the group consisting of lysine, lysine hydrochloride, lysine dihydrocholoride, lysine orotate, lysine succinate, and lysine glutamate, said lysine compound present in an amount of 100 mg;
   (d) B-carotene present in an amount of 100 mg; and
   (e) a pharmaceutically acceptable carrier.

5. A Pharmaceutical lysine-based composition for the treatment of cardiovascular disease consisting essentially of:
   (a) at least one ascorbate compound selected from the group consisting of ascorbic acid, pharmaceutically acceptable ascorbate salts and mixtures thereof, said ascorbate present in an amount of 400 mg;
   (b) nicotinic acid present in an amount of 100 mg;
   (c) at least one lysine compound selected from the group consisting of lysine, lysine hydrochloride, lysine dihydrocholoride, lysine orotate, lysine succinate, and lysine glutamate, said lysine compound present in an amount of 100 mg;
   (d) B-carotene present in an amount of 100 mg;
   (e) tocopherol present in an amount of 50 mg; and
   (f) a pharmaceutically acceptable carrier.

6. A method of treating cardiovascular disease by administering to a patient an effective dosage consisting essentially of:
   (a) at least one ascorbate compound selected from the group consisting of ascorbic acid, pharmaceutically acceptable ascorbate salts and mixtures thereof;
   (b) nicotinic acid;
   (c) at least one lysine compound selected from the group consisting of lysine, lysine hydrochloride, lysine dihydrocholoride, lysine orotate, lysine succinate, and lysine glutamate; and
   (d) a pharmaceutically acceptable carrier, said composition in an amount effective to treat cardiovascular disease.

* * * * *